(12) United States Patent
Almansour et al.

(10) Patent No.: US 9,486,444 B1
(45) Date of Patent: Nov. 8, 2016

(54) ANTI-CANCER COMPOUND (71) Applicant: KING SAUD UNIVERSITY, Riyadh (SA)

(72) Inventors: Abdulrahman I. Almansour, Riyadh (SA); Natarajan Arumugam, Riyadh (SA); Raju Suresh Kumar, Riyadh (SA); Periasamy Vaiyapuri Subbarayan, Riyadh (SA); Ali Abdullah Alshatwi, Riyadh (SA); Hazem A. Ghabbour, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 15/076,611

(22) Filed: Mar. 21, 2016

(51) Int. Cl.
A61K 31/40 (2006.01)
A61K 31/44 (2006.01)
C07D 401/00 (2006.01)
C07D 491/00 (2006.01)
A61K 31/435 (2006.01)

(52) U.S. Cl.
CPC .................. A61K 31/435 (2013.01)

(58) Field of Classification Search
None
See application file for complete search history.

(56) References Cited

U.S. PATENT DOCUMENTS

| 6,664,272 | B2 | 12/2003 | Snyder et al. |
| 8,629,133 | B2 | 1/2014 | Sugimoto et al. |
| 2008/0312222 | A1 | 12/2008 | Borza et al. |
| 2011/0053949 | A1 | 3/2011 | Meyers et al. |
| 2011/0144159 | A1 | 6/2011 | Fay et al. |

FOREIGN PATENT DOCUMENTS

| CN | 102863376 A | 1/2013 |
| CN | 104262240 A | 1/2015 |

OTHER PUBLICATIONS

Arumugam et al. Tetrahedron Letters 54 (2013) 2515-2519.*
Weintraub et al., "Recent advances in the synthesis of piperdones and piperidines," Tetrahedron, 2003, vol. 59, pp. 2953-2989.
Kálai et al., "Synthesis of N-substituted 3,5-bis(arylidene)-4-piperidones with high antitumor and antioxidant activity," J. Med. Chem., 2011, vol. 54, pp. 5414-5421.

* cited by examiner

Primary Examiner — Jeffrey S Lundgren
Assistant Examiner — Michael Schmitt
(74) Attorney, Agent, or Firm — Richard C. Litman (57) ABSTRACT Anti-cancer compounds include N-arylmethylidene piperidones having structural formula I:

FORMULA I

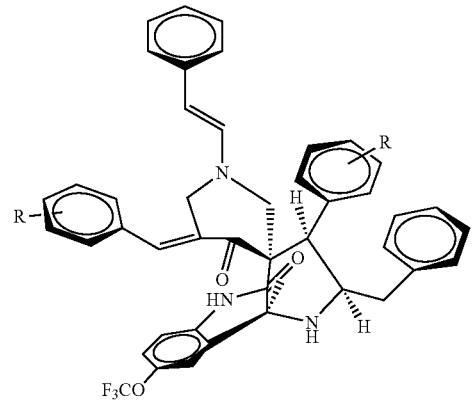

where R is a hydrogen, halogen, methyl, methoxy, or nitro group, or a pharmaceutically acceptable salt thereof.

11 Claims, 6 Drawing Sheets

ANTI-CANCER COMPOUND

BACKGROUND OF THE INVENTION

1. Field of the Invention

The present invention relates to anticancer agents, and particularly to an N-arylmethylidene piperidone tethered dispiropyrrolidine which induces apoptosis in blood cancer cells.

2. Description of the Related Art

Chemotherapy is a category of cancer treatment that uses chemical substances, especially one or more anti-cancer drugs (chemotherapeutic agents), that are given as part of a standardized chemotherapy regimen. Traditional chemotherapeutic agents are cytotoxic; i.e., they act by killing cells that divide rapidly, one of the main properties of most cancer cells. This means that chemotherapy also harms cells that divide rapidly under normal circumstances, such as the cells in the patient's bone marrow, digestive tract and hair follicles. This results in the most common side-effects of chemotherapy, namely, myelosuppression (i.e., decreased production of blood cells, hence also immunosuppression), mucositis (i.e., inflammation of the lining of the digestive tract), and alopecia (i.e., hair loss).

Some newer anticancer drugs (for example, various monoclonal antibodies) are not indiscriminately cytotoxic, but rather target proteins that are abnormally expressed in cancer cells and that are essential for their growth. Such treatments are often referred to as targeted therapy (as distinct from classic chemotherapy) and are often used alongside traditional chemotherapeutic agents in antineoplastic treatment regimens. There is a great deal of interest in targeted cancer treatments which induce apoptosis in targeted cancer cells.

Apoptosis, autophagy and necro-apoptosis are different kinds of programmed cell death (PCD) and a physiological mechanism by which cells with irreparably damaged DNA are removed without any inflammatory response. A growing body of evidence suggests that more than twenty different pathways contribute to different modes of cell death in tumor cells. Particularly, death domain receptors, DNA damage and repair, extracellular apoptotic signals, pro-apoptotic genes, anti-apoptotic, positive and negative apoptotic regulatory genes, death domain receptors and caspases and regulators are functional pathways involved, and play a key role in tumor pathophysiology.

In the pathway towards the induction of cancer, evading specific PCD (i.e., apoptosis) is one of the fundamental mechanisms. The direct molecular link between cancer pathogenesis and dysregulation of PCD are interlinked mechanisms that can be used as therapeutic targets by triggering PCD mechanisms (i.e., induced apoptosis) in tumor/cancer cells. Thus, screening by induction of apoptosis has potential application in target-based cancer therapy, which is one of the desired endpoints in cancer therapy. It would be desirable to be able to easily and effectively produce targeted PCD compounds for destroying desired cancer cells without causing damage to healthy cells in the patient. Thus, anti-cancer compounds solving the aforementioned problems are desired.

SUMMARY OF THE INVENTION

The anti-cancer compounds include N-arylidenepiperidone tethered dispiropyrrolidines having the following structural formula:

where R is hydrogen, halogen, methyl, methoxy, or a nitro group. An exemplary anti-cancer compound includes 5'-benzyl-4'-(p-tolyl)-5-(trifluoromethoxy)spiro[3,2']oxindolopyrrolidino-4'-(methylphenyl)-1"-styryl-5-benzylidene-spiro[3'.3"]piperidi-4"-one. The anti-cancer compounds can be useful as apoptosis inducers.

These and other features of the present invention will become readily apparent upon further review of the following specification.

BRIEF DESCRIPTION OF THE DRAWINGS

Similar reference characters denote corresponding features consistently throughout the attached drawings.

DETAILED DESCRIPTION OF THE PREFERRED EMBODIMENTS

Anti-cancer compounds include compounds having structural formula I:

FORMULA I where R is a hydrogen, halogen, methyl, methoxy, or nitro group, or a pharmaceutically acceptable salt thereof.

A pharmaceutically acceptable salt includes any non-toxic salt of the present compounds, which are generally prepared by reacting the free acid with a suitable organic or inorganic base. Examples of such salts include, but are not limited to, acetate, benzenesulfonate, benzoate, bicarbonate, bisulfate, bitartrate, borate, bromide, calcium, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylbromide, methyinitrate, methylsulfate, mucate, napsylate, nitrate, oleate, oxalate, pamaote, palmitate, panthothenate, phosphate/diphosphate, polygalacturonate, potassium, salicylate, sodium, stearate, subacetate, succinate, tannate, tartrate, teoclate, tosylate, triethiodide, valerate.

Acids with which addition salts can be formed can include hydrohalic acids such as for example, hydrochloric acid and hydrobromic acid, and also phosphoric acid, nitric acid, monofunctional and bifunctional carboxylic acids hydroxy carboxylic acids, such as, acetic acid, maleic acid, succinic acid, fumaric acid, tartaric acid, salicylic acid, sorbic acid and lactic acid, as well as sulphonic acids such as, p-toluenesulphonic acid and naphthaline-1,5-disulphonic acid.

The anti-cancer compounds can be used as an active ingredient in a pharmaceutical composition for the treatment of proliferative diseases, such as cancer, and particularly blood cancer. It has previously been reported that compounds possessing bis-arylidene piperidinone derivatives displayed excellent anti-cancer activity and that the cytotoxic activity was due to the presence of bis-arylidene structural motif (S. Das, U. Das, D. Michel, D. K. J. Gorecki, J. R. Dimmock, Eur. J. Med. Chem. 2013, 64, 321-328). The pharmaceutical composition can include a compound of the present invention and a pharmaceutically acceptable carrier, diluent or excipient. The compound can be in an "effective amount" to elicit the biological or medical response of a tissue, system, animal or human that is being sought by the researcher, veterinarian, medical doctor or other clinician. As would be understood by those skilled in the art of treating cancer, the term "treatment" does not necessarily mean that the cancer is completely cured. The term "treatment" encompasses any inhibition of replication of cancer cells and/or reduction in the tumor size in the subject being treated.

Figure 3:
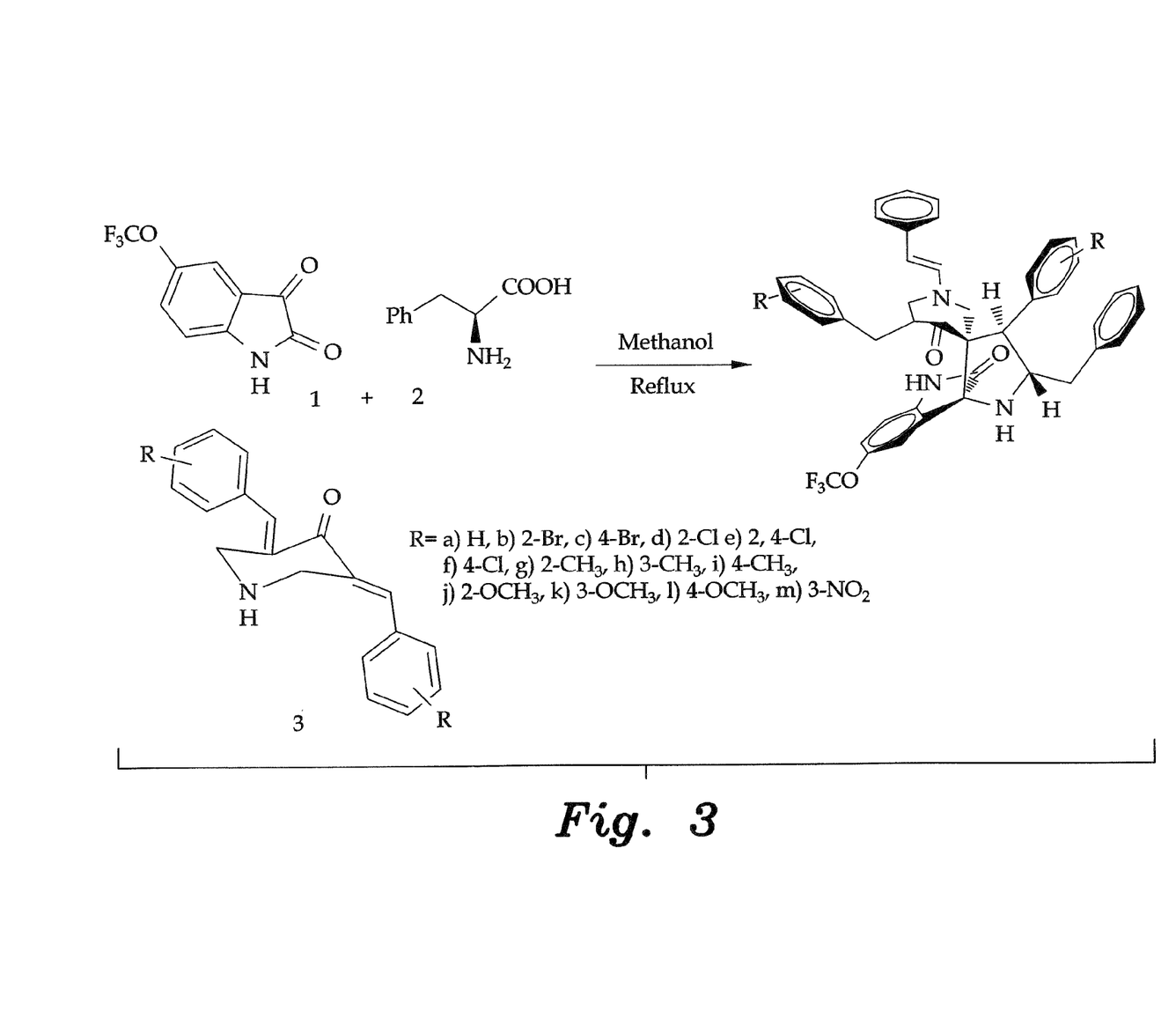
FIG. 3 is the reaction scheme for synthesis of the anti-cancer compound according to the present invention.
Figure 4:
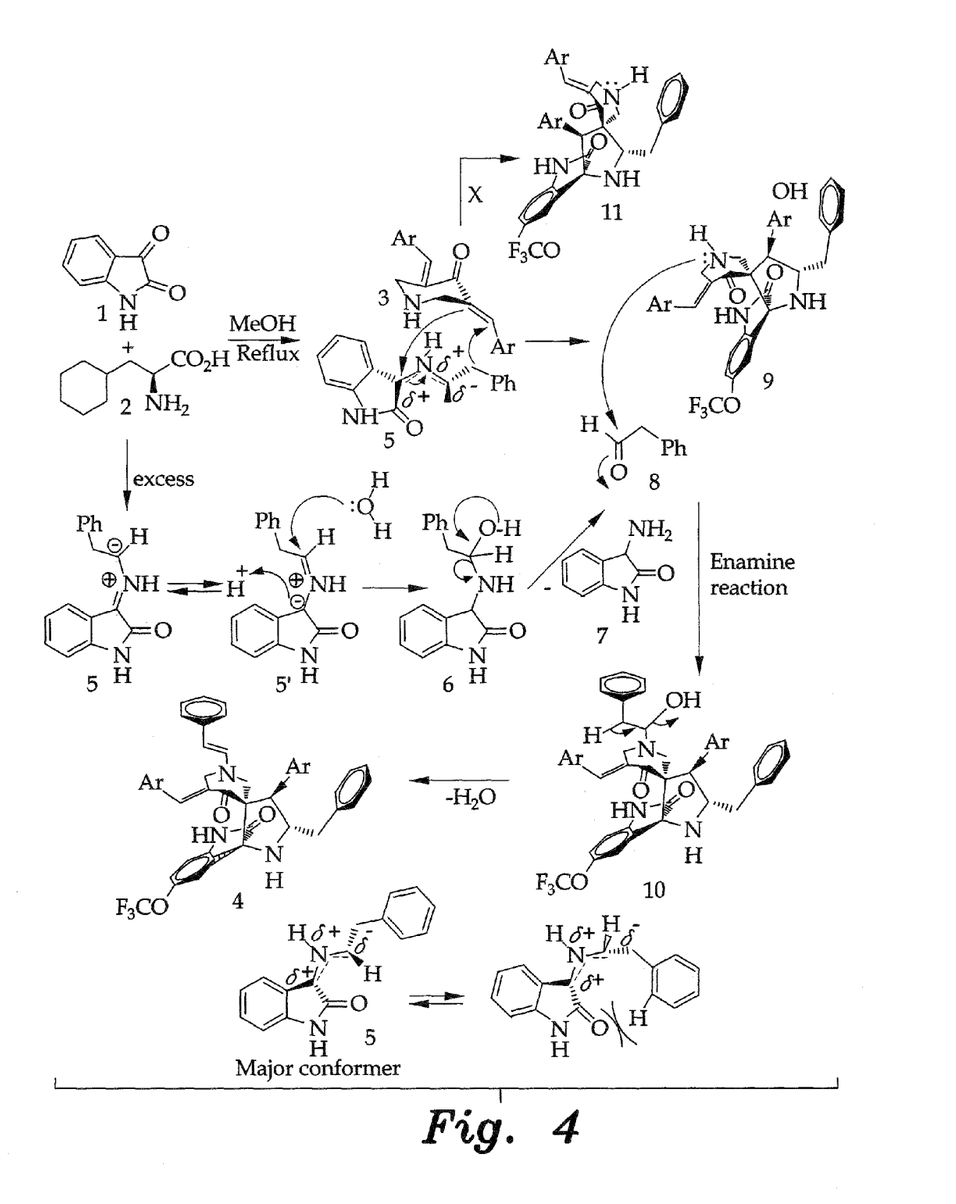
FIG. 4 is a more detailed diagram indicating the probable mechanism for the formation of the anti-cancer compound shown in FIG. 3.

The anti-cancer compounds can be synthesized based on a three-component reaction strategy, as illustrated in FIGS. 3 and 4, which includes a domino process comprising, 1,3-dipolar cycloaddition reaction between (3E,5E)-3,5-bis (4-methylbenzylidene)piperidin-4-one and azomethine ylide (5) generated in situ from isatin (1) and L-phenylalanine (2) to afford spiroheterocycle (9), which subsequently reacts with 2-phenylacetaldehyde (8), generated in situ from azomethine ylide, to afford the N-substituted arylmethylidene piperidone tethered dispiropyrrolidine (4) through an enamine formation reaction (FIG. 4).

A plausible mechanism for the formation of the N-substituted piperidinone tethered spirooxindolopyrrolidine through domino transformation is shown in FIG. 4. Presumably, the reaction of isatin (1) and L-phenylalanine (2) affords azomethine ylide (5) via decarboxylative condensation. This intermediate then adds regioselectively to one of the C=C bonds of (3) with the nucleophilic benzyl carbon of the azomethine ylide adding to the electron-deficient β-carbon of the azomethine ylide to form the cycloadduct (9). The other possible regioisomer of (9), i.e., compound 11, was not formed. The regiochemical outcome is also in accord with steric factors as well as possible secondary orbital interactions between the nitrogen lone pair and the carbonyl function during the cycloaddition favoring the formation of (9). Simultaneously, the azomethine ylide (5') was attacked by water molecule to furnish 2-phenylacetaldehyde (8) and 3-aminoindolin-2-one (7) as a byproduct via compound (6). Subsequently, 2-phenylacetaldehyde was attacked by nitrogen lone pair of (9) to form (10) through enamine reaction followed by dehydration to afford the N-arylidene piperidinone tethered spiropyrrolidine (4).

A series of thirteen N-arylidene piperidinone tethered spiropyrrolidines (compounds 4a-m) of structural Formula I, were synthesized according to the methods described herein. The various N-arylidene piperidinone tethered spiropyrrolidines (compounds 4a-m) are provided below in Table 1.

TABLE 1

| Compounds | R |
| --- | --- |
| 4a | H |
| 4b | 2-Br |
| 4c | 4-Br |
| 4d | 2-Cl |
| 4e | 2,4-Cl |
| 4f | 4-Cl |
| 4g | 2-$CH_3$ |
| 4h | 3-$CH_3$ |
| 4i | 4-$CH_3$ |
| 4j | 2-$OCH_3$ |
| 4k | 3-$OCH_3$ |
| 4l | 4-$OCH_3$ |
| 4m | 3-$NO_2$ |

Apoptotic cell death is one of the advocated modalities for the therapy of cancer in induction of cell death through therapeutic interventions. Cytotoxicity of the 13 separate N-arylmethylidene piperidone tethered spiropyrrolidines (4a-4m) against the U-937 blood cancer was assessed by the present inventors using fluorescent microscopic techniques to assess the mode of cell death, and to elucidate whether cells die of apoptosis or through alternative processes. It was found that compounds 4a-4m induced an increase in the percentage of early apoptotic cells (green fluorescing nuclei, but the peri-nuclear chromatin condensation was visible as bright green patches or fragments) and late apoptotic cells (orange-red fluorescing nuclei with condensed or fragmented chromatin).

It was determined that of the compounds 4a-4m, the most cytotoxic compound was compound (4i), or 5'-benzyl-4'-(p-tolyl)-5-(trifluoromethoxy)spiro[3,2']oxindolopyrrolidino-4'-(methylphenyl)-1''-styryl-5-benzylidene-spiro[3'.3'']piperidi-4''-one. The cytotoxicity of the compounds (4a-4m) cell line was investigated in comparison with the widely used drug bleomycin under identical conditions by using an MTT assay for 24 and 48 hours (results shown in FIG. 5). The ability of the compounds (4a-m) to exhibit cytotoxicity was found to follow the order (4i<4m<4g<4h<4j<4e<4k<4l<4f<4d<4b<4c<4a). The observed $IC_{50}$ values revealed that the compounds (4a-4m) exhibit cytotoxicity slightly above that of bleomycin ($IC_{50}$=16.2±4.5) for a 24 hour incubation time.

Accordingly, compounds 4a-4m bring about nuclear fragmentation in cancer cells and morphological analysis provides very strong evidence in support of apoptosis as the mechanism of cell death in the context of compounds (4a-4m) treatment.

The following examples illustrate the present teachings.

Example 1

In order to make the anti-cancer compounds, 40 wt % of 5-(trifluoromethoxy)indoline-2,3-dione (2.72 mmol), 40 wt % of L-phenylalanine (2.72 mmol) and 20 wt % of (3E,5E)-3,5-bis(4-methylbenzylidene)piperidin-4-one (1.36 mmol) were mixed to form a mixture. The mixture was refluxed in methanol for two hours. After completion of the reaction, as evidenced from thin layer chromatography (TLC), the reaction mixture was cooled to room temperature. This caused a white solid to slowly precipitate out in the bottom of the flask. Excess methanol was decanted and the crude product was washed with cold ethyl acetate (2 mL×5). The product was dried under reduced pressure to afford the cycloadducts (compounds 4a-4m) in excellent yields.

Further purification was performed by crystallizing the precipitate in ethyl acetate by slow evaporation techniques. The product compound (20 mg) in ethyl acetate (3 mL) was heated to 80° C., and the hot solution was then filtered. The product filtrate was held for 72 hours at room temperature, producing the purified compound, in the form of colorless crystals.

Optimization for this domino reaction was performed in different organic solvents. As a representative case, initially the reaction was performed with an equimolar mixture of (3E,5E)-3,5-bis(4-methylbenzylidene)piperidin-4-one, isatin and L-phenylalanine in methanol. The reaction afforded the product only in 25% yield even after 10 hours under reflux. The starting precursor (3) was still present in the reaction mixture, as evidenced by TLC. The same reaction was performed with (3E,5E)-3,5-bis(4-methylbenzylidene)piperidin-4-one (1 equiv.), isatin (2 equiv.) and L-phenylalanine (2.05 equiv.), and the reaction progress was monitored every 30 minutes. The reaction was completed in 2 hours (TLC), affording the product in good yield. The reaction was also performed under reflux in different solvents, viz dioxane, dioxane/methanol (1:1 v/v) mixture, toluene, and acetonitrile. In all reactions, the N-arylidene piperidone tethered dispiropyrrolidine (4) was formed only in moderate yields, even after long reaction times. The best results were obtained only in heating the reaction mixture to reflux in methanol for 2 hours to afford the product as a single regioisomer in good yield. Consequently, all subsequent reactions were performed under this optimized reaction condition. A series of thirteen N-arylidene piperidone tethered dispiropyrrolidine (4) were synthesized. The structures of newly synthesized spiro compounds were elucidated using spectroscopic studies. Finally, the structure and stereochemistry of cycloadduct (4) was elucidated unambiguously by a single crystal X-ray diffraction study of compound 4i.

The structure of the synthesized compounds 4a-4m was elucidated using IR, Mass, $^1$H, $^{13}$C and 2D NMR spectroscopic data, as illustrated for compound 4i: For compound 4i (5'-benzyl-4'-(p-tolyl)-5-(trifluoromethoxy)spiro[3,2']oxindolopyrrolidino-4'-(methylphenyl)-1''-styryl-5-benzylidene-spiro[3'.3'']piperidi-4''-one): Colorless crystals, 90%; $^1$H NMR (CDCl$_3$, 400 MHz): δ/ppm $^1$H NMR (CDCl$_3$, 400 MHz): δ/ppm 5.00 (d, J=14.5 Hz, 1H), 4.66-4.70 (m, 1H), 4.30 (d, J=10.0 Hz, 1H), 3.77 (d, J=14.00 Hz, 1H), 3.67 (d, J=15.00 Hz, 1H), 3.41-3.50 (dd, J=15 Hz, 1H), 3.00-3.04 (dd, J=14.5 Hz, 1H), 2.70-2.75 (m, 1H), 2.55 (d, J=14.0 Hz, 1H), 2.35 (s, 3H), 2.32 (s, 3H), 6.52 (d, J=14.5 Hz, 1H), 6.58-7.48 (m, 21H, Ar); $^{13}$C NMR (CDCl$_3$, 100 MHz): δ/ppm 21.06, 21.44, 39.48, 47.36, 52.76, 52.90, 61.09, 66.99, 70.79, 100.70, 109.56, 119.47, 120.96, 121.52, 122.32, 123.97, 124.23, 126.31, 128.37, 128.47, 129.18, 129.35, 129.38, 130.47, 131.62, 133.69, 136.87, 138.27, 138.39, 138.71, 139.60, 139.78. 140.00, 144.29, 179.83, 197.06. EI-MS: m/z 739 (M$^+$). Anal. Calcd for C$_{46}$H$_{40}$F$_3$N$_3$O$_3$: C, 74.68; H, 5.45; N, 5.68. Found: C, 74.76; H, 5.53; N, 5.79.

Figure 1:
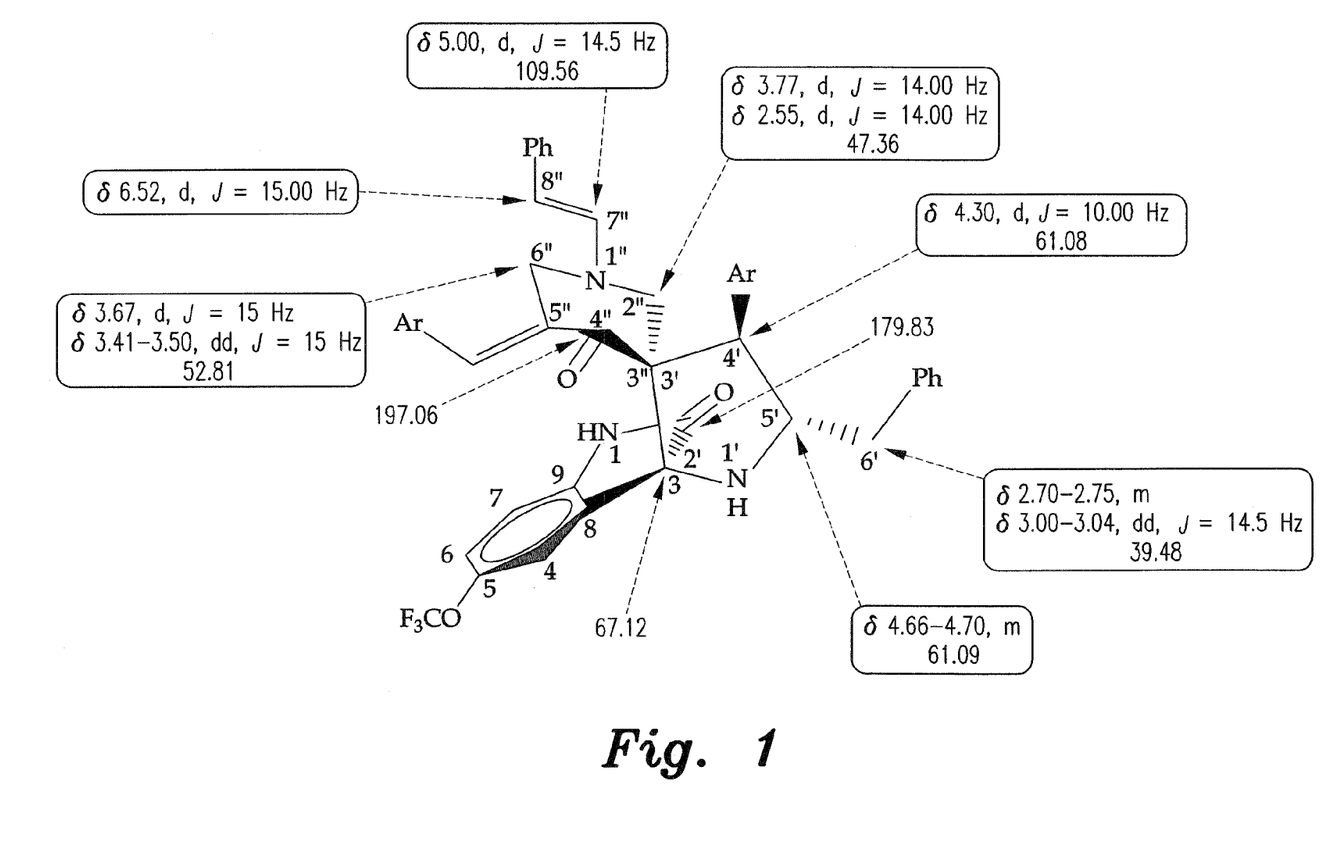
FIG. 1 is a diagram illustrating $^1$H and $^{13}$C chemical shifts of an anti-cancer compound according to the present invention.
Figure 2:
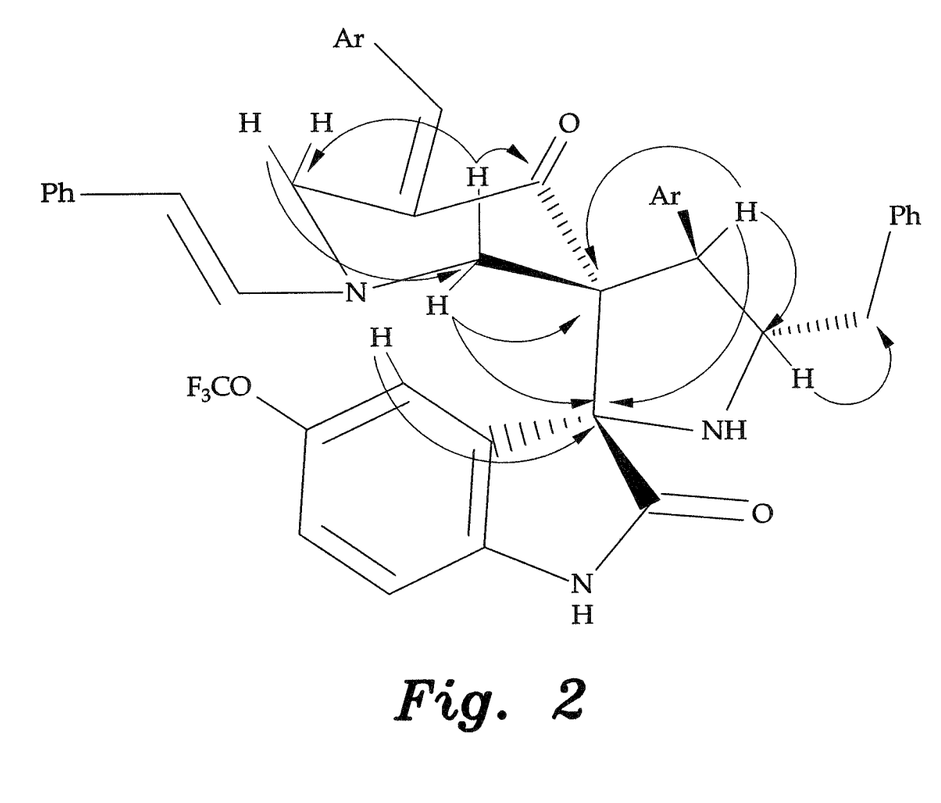
FIG. 2 is a diagram illustrating heteronuclear multiple bond correlations (HMBCs) of the anti-cancer compound of FIG. 1.

The IR spectrum of compound 4i showed absorptions at 1614 and 1708 cm$^{-1}$, assignable to piperidone and oxindole carbonyls respectively. The $^1$H NMR spectrum of the present compound has a doublet at δ 4.30 ppm (J=10.00 Hz) for benzylic proton 4'-CH of the pyrrolidine ring, which shows HMBCs with spiro carbon C-3' at 70.79 ppm and the methine carbon C-5' at 61.09 ppm. The multiplet at δ 4.66-4.70 ppm was assigned to 5'-CH based on its H, H-COSY correlation with 4'-CH. Further, the multiplet at δ 2.70-2.75 and doublet of doublets 3.00-3.04 ppm (J=14.5 Hz) were assigned to 6'-CH$_2$ as it shows H, H-COSY correlation with 5'-CH. From H, H-COSY correlations, the two doublets at δ 3.77 and 2.55 ppm (J=14.00 Hz) can be assigned to 2''-CH$_2$ hydrogens, as it shows HMBCs with C-2' at 67.12 and C-3' at 70.79 ppm, besides showing a correlation with piperidinone carbonyl carbon at 197.06 ppm.

The arylmethylidene proton 7''-CH appeared as a doublet at δ 5.00 ppm (J=14.50 Hz), while 8''-CH exhibited as a doublet at δ 6.52 ppm (J=15.00 Hz). The signal assignments are consistent with the HMBCs and H, H-COSY correlation depicted in FIG. 2. The fact that the H-4' benzylic proton appeared as a doublet at δ 4.31 ppm (J=11.0 Hz) clearly establishes the regiochemistry of the cycloaddition, as for the other possible regiomers that might have arisen from the cyloaddition, it should give a singlet. In the $^{13}$C NMR spectrum, the signals at 70.83 and 67.12 ppm were attributed to C-3' and C-2' carbons, respectively, while the signals at 39.48, 47.36 and 52.81 ppm were assigned to the three methylene carbons (C-6', C-2'' and C-6''). The signals at 179.83 and 197.06 were due to oxindole and piperidone carbonyl carbon, respectively, as shown in FIG. 1. The carbon chemical shifts of C-2'', C-6', C-6'', C-2', C-3', C-4' and C-5' were also confirmed from DEPT-135 spectroscopic analysis. Furthermore, the presence of a molecular ion peak at m/z=739 (M$^+$) in the mass spectrum of the present compound confirms the formation of a spiroheterocyclic hybrid. The structure of other spiropyrolidines was also assigned by similar straight forward considerations.

Single crystal X-ray diffraction analysis showed that the N-arylmethylidene piperidone (Compound 4i) is composed of a central pyrrolidine ring (C8/N4/C9-C11) with benzyl group (C17-C23) at C9, p-tolyl (C24-C30) at C10, spiro-connections with indolin-2-one at C8 and a 2,3-piperidinone ring at C11. The dihedral angle between the pyrrolidine ring A (C8/N4/C9-C11), indolin-2-one ring B (C1-C8/N3) and piperidinone ring C (C11-C15/N) are 97.27 (2)° and 87.90 (3)° 39.64(2)° for A/B, A/C and B/C, respectively. In the crystal structure, two intermolecular NH—H...O and C—H...O hydrogen bonds are observed N3-H1N3...O2 and C41-H41A...O3. The selected geometric parameters and distances of the donor-H, acceptor/H, donor/acceptor and donor-H/acceptor angles are presented in Tables 2A, 2B and 3.

TABLE 2A

Bond distances and angles in blood cancer treatment composition (Å, (°))

| | |
|---|---|
| F1—C16 | 1.318 (3) |
| F2—C16 | 1.297 (4) |
| F3—C16 | 1.287 (5) |
| O1—C5 | 1.415 (3) |
| O1—C16 | 1.284 (4) |
| O2—C1 | 1.224 (2) |
| O3—C15 | 1.213 (2) |
| C5—O1—C16 | 121.7 (2) |
| C12—N1—C13 | 118.85 (14) |
| C12—N1—C31 | 119.42 (15) |
| C13—N1—C31 | 118.99 (16) |
| C1—N3—C2 | 111.73 (16) |
| C8—N4—C9 | 109.34 (16) |
| O2—C1—N3 | 125.63 (17) |
| O2—C1—C8 | 125.90 (17) |
| N3—C1—C8 | 108.40 (15) |
| N3—C2—C3 | 128.86 (18) |
| N3—C2—C7 | 109.58 (17) |
| O1—C5—C4 | 114.7 (2) |
| O1—C5—C6 | 122.9 (2) |
| N4—C8—C1 | 113.66 (15) |
| N4—C8—C7 | 111.03 (15) |

TABLE 2B

Bond distances and angles in blood cancer treatment composition (Å, (°))

| | |
|---|---|
| N1—C12 | 1.445 (3) |
| N1—C13 | 1.453 (2) |
| N1—C31 | 1.371 (2) |
| N3—C1 | 1.356 (3) |
| N3—C2 | 1.397 (2) |
| N4—C8 | 1.453 (3) |
| N4—C9 | 1.457 (3) |
| N4—C8—C11 | 102.34 (14) |
| N4—C9—C17 | 108.54 (16) |
| N4—C9—C10 | 100.52 (15) |
| N1—C12—C11 | 110.38 (15) |
| N1—C13—C14 | 113.80 (16) |
| O3—C15—C14 | 121.63 (17) |
| O3—C15—C11 | 121.34 (18) |
| F2—C16—O1 | 111.9 (3) |
| F3—C16—O1 | 112.5 (3) |
| F1—C16—F3 | 106.6 (2) |
| F1—C16—O1 | 109.1 (3) |
| F1—C16—F2 | 109.1 (3) |
| F2—C16—F3 | 107.6 (3) |
| N1—C31—C32 | 127.44 (18) |

TABLE 3

Hydrogen-bond geometry (Å, (°))

| D—H...A | D—H | H...A | D...A | D—H...A |
|---|---|---|---|---|
| N3—H1N3...O2[i] | 0.89 (2) | 1.99 (2) | 2.879 (2) | 174 (2) |
| C41—H41A...O3[ii] | 0.9300 | 2.5800 | 3.353 (3) | 141.00 |

Symmetry codes: [i] $-x + 1, -y + 1, -z$; [ii] $-x, -y + 1, -z + 1$

For the X-ray crystallographic analysis, a clear light yellow plate-like crystal of $C_{36}H_{30}FN_4O_3$ (approximate dimensions of 0.52×0.35×0.09 mm) was used. A total of 684 frames were collected. The total exposure time was 2.85 hours. The integration of the data using a unit cell, space group P-1, yielded a total of 40,552 reflections to a maximum θ angle of 26.4°, of which 7,898 were independent (completeness=99.7%, $R_{int}$=2.9%) and 5,984 were greater than $2\sigma(F^2)$. The final cell constants of a=10.9564 (3) Å, b=12.8673 (3) Å, c=15.8159 (4) Å, α=66.747 (1)°, β=73.551 (1)°, γ=74.505 (1)°, volume=1933.97 (9) Å$^3$, were based upon the refinement of the XYZ-centroids of 9,790 reflections above 20 σ(I) with 4.8°<2θ<52.8°. Data were corrected for absorption effects using the multi-scan method (SADABS). The goodness-of-fit was 1.036. The largest peak in the final difference electron density synthesis was 0.55 e-/Å$^3$ and the largest hole was −0.53 e-/Å$^3$. On the basis of the final model, the calculated density was 2.011 g/cm$^3$ and F(000)=1,228.

Example 2

For cytotoxicity assays, the anti-cancer compounds were prepared as a stock solution, to suit a universal 96 well plate map, at different concentrations in µM, and dissolved in DMSO dH$_2$O. Working solutions were prepared in the culture medium and added to the wells 24 hours after seeding of 5 to 7×103 cells per well in 200 µL of fresh culture medium. DMSO (1%)/dH$_2$O was used as the solvent control. The DMSO concentration was maintained at a concentration less than 1% (i.e., a non-toxic concentration). Microscopic cytological changes were monitored and photographed following exposure to different concentrations of the compounds for 24 and 48 hours using an inverted microscope. After the respective periods of treatment, plates were centrifuged and washed with fresh growth medium. Then, 20 µL of MTT solution [5 mg/mL in phosphate-buffered saline (PBS)] was added to each well, and the plates were wrapped with aluminum foil and incubated overnight at 37° C. The plates were centrifuged and the supernatants were removed carefully via distribution of formazan products. The purple formazan product was dissolved in 100 µL of 100% DMSO. The absorbance was monitored at 570 nm (measurement) and 630 nm (reference) using a 96 well plate reader. Data were collected for four replicates each and used to calculate the median effect dose or concentration; i.e., IC$_{50}$.

Acridine orange (AO) and ethidium bromide (EB) fluorescent probes were used for assessment of cell death. The cells (5×105) were incubated with acridine orange and ethidium bromide solution (1 part each of 100 µg/mL acridine orange and ethidium bromide in PBS) and mixed gently, and examined in a fluorescent microscope using a UV filter (450-490 nm). Three hundred cells per sample were counted in triplicate for each dose point. Cells were scored as viable, apoptotic or necrotic, as judged from nuclear morphology and membrane integrity, and the respective percentages of apoptotic and necrotic cells were then calculated. The cells of interest were photographed.

Double fluorescent staining of acridine orange (AO) and ethidium bromide (EB) was used. Thus, the cells were classified into five types according to the fluorescence emission and the morphological feature of chromatin condensation in the stained nuclei: (i) Viable cells had uniformly green fluorescing nuclei with a highly organized structure; (ii) early apoptotic cells have green fluorescing nuclei, but the peri-nuclear chromatin condensation was visible as bright green patches or fragments; (iii) late apoptotic cells had orange-red fluorescing nuclei with condensed or fragmented chromatin; (iv) necrotic cells have uniformly red nucleus and cytoplasm; and (v) red and/or green stained cells with non-apoptotic morphological features; i.e., fragmented nuclei with original cell morphology, vacuolated cytoplasm, cytoplsmic lesion, etc., indicating that the terminal point in necro-apoptosis has reached. Fluorescent images of the present compound's induced morphological features were observed using a high efficiency fluorescent microscope with apoptome fitted with time-lap and imaging facilities. The data presented below are representative of those obtained in at least three independent experiments conducted in triplicate.

Cytotoxicity of the 13 separate N-arylmethylidene piperidone tethered spiropyrrolidines was assessed, with the most cytotoxic compound being compound (4i), where R=4-CH$_3$, thus forming 5'-benzyl-4'-(p-tolyl)-5-(trifluoromethoxy)spiro[3,2']oxindolopyrrolidino-4'-(methylphenyl)-1"-styryl-5-benzylidene-spiro[3'.3"]piperidi-4"-one.

Figure 5:
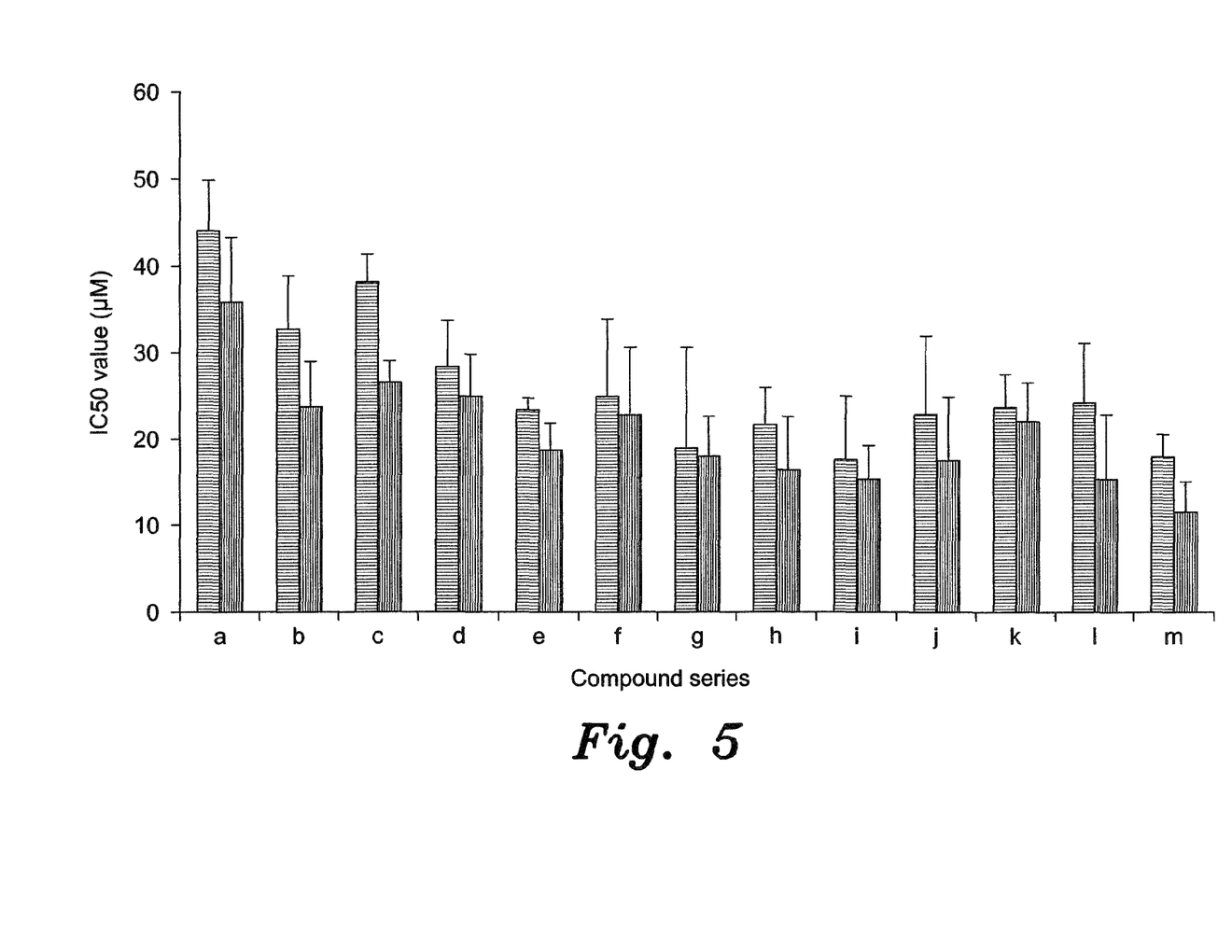
FIG. 5 is a graph comparing in vitro cytotoxicity assays for the 13 N-arylmethylidene piperidone tethered spiropyrrolidine anti-cancer compounds according to the present invention.

The cytotoxicity of compounds (4a-4m) against the U-937 blood cancer cell line was investigated in comparison with the widely used drug bleomycin under identical conditions by using an MTT assay for 24 and 48 hours (results shown in FIG. 5). The ability of the compounds (4a-m) to exhibit cytotoxicity follows the order (4i<4m<4g<4h<4j<4e<4k<4l<4f<4d<4b<4c<4a). The observed IC$_{50}$ values revealed that the compounds (4a-4m) exhibit cytotoxicity slightly above that of bleomycin (IC$_{50}$=16.2±4.5) for a 24 hour incubation time. It should be noted that the compounds (4i) and (4m), bearing para-methyl and meta-nitro moieties on aromatic rings, respectively, displayed excellent cytotoxicity effects at the lowest concentrations among the 13 different compounds. In general, methyl and methoxy substituted derivatives viz., (4g) with o-methyl, (4h) with m-methyl, (4j) with o-methoxy, (4e) with m-methoxy and p-methoxy moiety on the phenyl rings displayed good cytotoxicity. Among the derivatives with halogen substituents in the phenyl ring, compound (4e), with a 2,4-dichloro substituent, showed good activity than other halogen derivatives. FIG. 5 shows the results of the in vitro cytotoxicity assays for compounds (4a-m) against the U-937 blood cancer cell line, where the data are mean±SD of four replicates each. In FIG. 5, the lighter bars (for compounds a-m) represent results after 24 hours, and the darker bars represent results after 48 hours. Here, IC$_{50}$=concentration (μM) of drug required to inhibit growth of 50% of the cancer cells.

The morphology of the cells treated with the compounds (4a-4m) was used to determine the extent and nature of the cytological effects. A routine dual staining technique (AO and EB staining) was employed, which indicated the changes in the overall profile of the cell, with special reference to the cytoplasm and the nuclear morphology. AO and EB staining and fluorescence microscopy revealed apoptosis from the perspective of fluorescence. After the cells were exposed to IC$_{50}$ concentrations of the compounds (4a-4m) for 24 and 48 hours, the cells were classified into four types according to the fluorescence emission and the nature of chromatin condensation in the nuclei as follows: (i) viable cells had uniformly green fluorescing nuclei with a highly organized structure; (ii) early apoptotic cells (which still had intact membranes but had started undergoing DNA fragmentation) had green fluorescing nuclei, but peri-nuclear chromatin condensation was visible as bright green patches or fragments; (iii) late apoptotic cells had orange to red fluorescing nuclei with condensed or fragmented chromatin; and (iv) necrotic cells had uniformly orange to red fluorescing nuclei with no indication of chromatin fragmentation but the cells were swollen to a large size.

Figure 6:
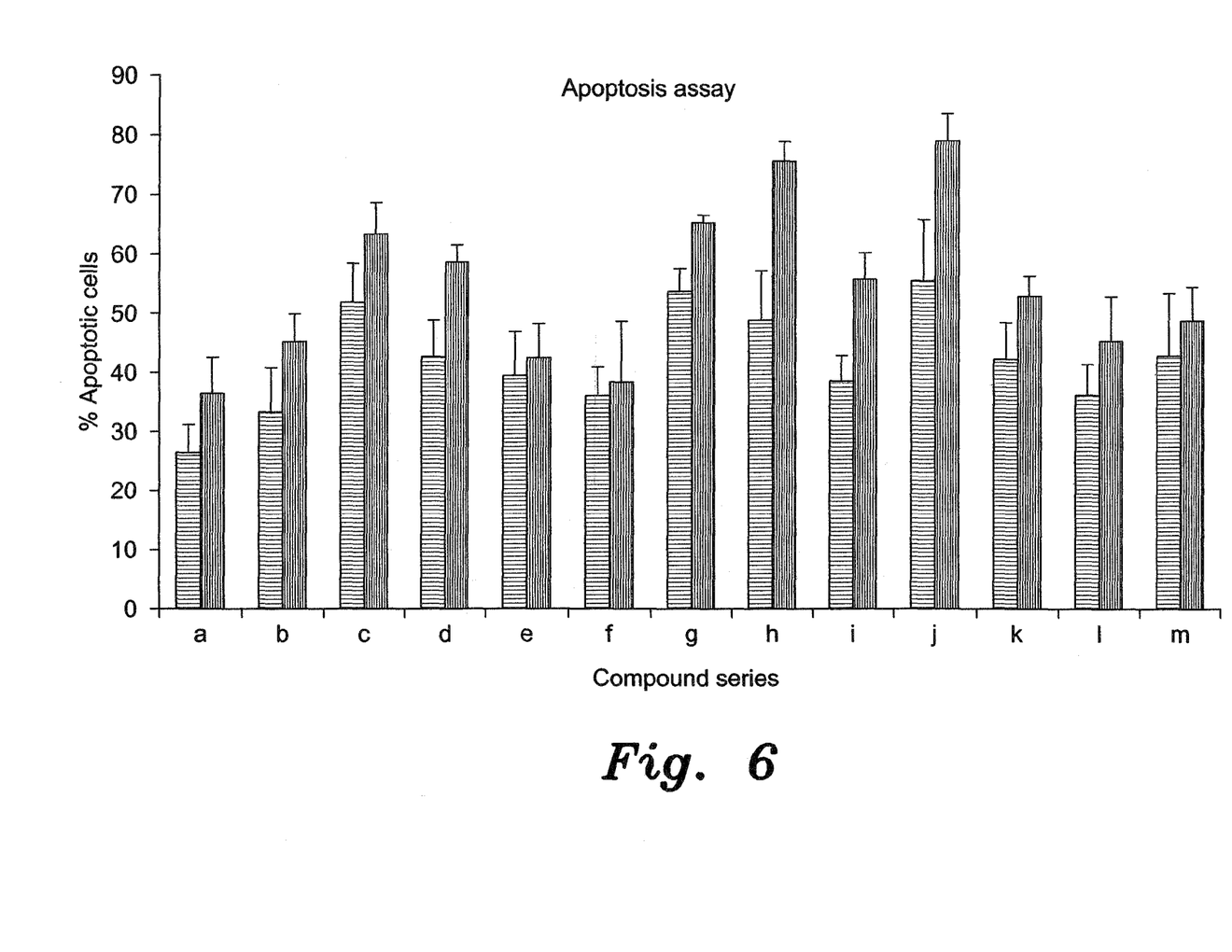
FIG. 6 is a graph comparing morphological data related to apoptosis of blood cancer cells (U-937) for the 13 N-arylmethylidene piperidone anti-cancer compounds according to the present invention.

The results indicated that treatment with the compounds (4a-4m) caused more cells to take to apoptosis morphologies than necrotic features in dose and time-dependent manners. Considering apoptosis in isolation, its incidence had a similar effect for all compounds. The data clearly showed that the changes induced by the compounds (4a-4m) were consistent with the induction of both apoptotic cell death. Overall, the compounds (4j>4h>4g>4c>4d>4i>4k>4m>4l>4b>4e>4f>4a) under assay on U-937 blood cancer cells indicated higher incidence of apoptosis for 48 hours. It would appear that the mode of cell death was dependent on the concentration and incubation time, see e.g., AO & EB stained U-937 cancer cells treated with compound 4i (a-untreated; b-dose IC$_{25}$; c-IC$_{50}$, and d-IC$_{75}$) for 24 hours, 400×). It was also indicated that the cells required short to longer incubation time for death only by apoptosis than necrosis. In other words, the early response was death by apoptosis, and the cells which did not die by apoptosis later succumbed to necrosis upon short to prolonged treatment with the compounds (4a-4m). FIG. 6 illustrates the AO/EB morphological data, showing the response of the cancer cells, in terms of apoptosis, to the compounds (4a-4m). The percentage of cells in apoptosis is indicated by the histograms. The data shown are the means from triplicates. Vertical bars represent standard error of mean. As with FIG. 5, in FIG. 6, the lighter bars (for compounds 4a-m) represent results after 24 hours, and the darker bars represent results after 48 hours.

It is to be understood that the present invention is not limited to the embodiments described above, but encompasses any and all embodiments within the scope of the following claims.

We claim:

1. An anti-cancer compound, comprising an N-arylmethylidene piperidone having the structure:

wherein R is selected from the group consisting of a hydrogen, halogen, methyl, methoxy, and nitro group, or a pharmaceutically acceptable salt thereof.

2. The anti-cancer compound according to claim 1, wherein the N-arylmethylidene piperidone comprises 5'-benzyl-4'-(p-tolyl)-5-(trifluoromethoxy)spiro[3,2']oxindolopyrrolidino-4'-(methylphenyl)-1"-styryl-5-benzylidene-spiro[3'.3"]piperidi-4"-one.

3. The anti-cancer compound according to claim 1, wherein R is selected from the group consisting of H, Br, Cl, $CH_3$, $OCH_3$, and $NO_2$.

4. The anti-cancer compound according to claim 3, wherein R is selected from the group consisting of H, 2-Br, 4-Br, 2-Cl, 2,4-Cl, 4-Cl, 2-$CH_3$, 3-$CH_3$, 4-$CH_3$, 2-$OCH_3$, 3-$OCH_3$, 4-$OCH_3$, and 3-$NO_2$.

5. A method of making the anti-cancer compound according to claim 1, comprising the steps of:
    mixing 5-(trifluoromethoxy)indoline-2,3-dione, L-phenylalanine, and (3E,5E)-3,5-bis(4-methylbenzylidene)piperidin-4-one to form a mixture;
    refluxing the mixture; and
    cooling the mixture to form a precipitate.

6. The method of making the anti-cancer compound according to claim 5, wherein the mixture comprises 40 wt % of the 5-(trifluoromethoxy)indoline-2,3-dione, 40 wt % of the L-phenylalanine, and 20 wt % of the (3E,5E)-3,5-bis(4-methylbenzylidene)piperidin-4-one.

7. The method of making the anti-cancer compound according to claim 6, wherein the step of refluxing the mixture in methanol comprises refluxing the mixture in methanol for two hours.

8. The method of making the anti-cancer compound according to claim 7, further comprising the steps of:
    washing the precipitate in ethyl acetate; and
    drying the precipitate.

9. A method of treating cancer in a patient in need thereof comprising administering to said patient a therapeutically effective amount of the anti-cancer compound according to claim 1.

10. The method of treating cancer according to claim 9, wherein the cancer is blood cancer.

11. A pharmaceutical composition comprising the anti-cancer compound according to claim 1, and a pharmaceutically acceptable carrier, diluent or excipient.

* * * * *